US008617118B1

(12) United States Patent
Marks (10) Patent No.: US 8,617,118 B1
(45) Date of Patent: Dec. 31, 2013

(54) SAFETY NEEDLE AND METHOD OF MAKING SAME

(76) Inventor: Lloyd A. Marks, Westfield, NJ (US)

(*) Notice: Subject to any disclaimer, the term of this patent is extended or adjusted under 35 U.S.C. 154(b) by 980 days.

(21) Appl. No.: 12/264,618

(22) Filed: Nov. 4, 2008

(51) Int. Cl.
*A61M 5/00* (2006.01)
*A61M 5/32* (2006.01)
*A61M 5/178* (2006.01)

(52) U.S. Cl.
USPC ............. 604/192; 604/164.08; 604/263

(58) Field of Classification Search
USPC ............. 604/192–198, 110, 164.08, 187, 263
See application file for complete search history.

(56) References Cited

U.S. PATENT DOCUMENTS

| | | |
|---|---|---|
| 2,674,246 A | 4/1954 | Bower |
| 3,134,380 A | 5/1964 | Armao |
| 3,840,008 A | 10/1974 | Noiles |
| 4,139,009 A | 2/1979 | Alvarez |
| 4,725,267 A | 2/1988 | Vaillancourt |
| 4,735,618 A | 4/1988 | Hagen |
| 4,775,369 A | 10/1988 | Schwartz |
| 4,781,697 A | 11/1988 | Slaughter |
| 4,790,828 A | 12/1988 | Dombrowski et al. |
| 4,867,172 A | 9/1989 | Haber et al. |
| 4,887,998 A | 12/1989 | Martin et al. |
| 4,892,521 A | 1/1990 | Laico et al. |
| 4,897,083 A | 1/1990 | Martell |
| 4,898,589 A | 2/1990 | Dolgin et al. |
| 4,911,706 A | 3/1990 | Levitt |
| 4,915,697 A | 4/1990 | DuPont |
| 4,917,672 A | 4/1990 | Terndrup et al. |
| 4,935,013 A | 6/1990 | Haber et al. |
| 4,950,250 A | 8/1990 | Haber et al. |
| 4,955,866 A | 9/1990 | Corey |
| 4,978,344 A | 12/1990 | Dombrowski et al. |
| 4,998,922 A | 3/1991 | Kuracina et al. |
| 5,015,240 A | 5/1991 | Soproni et al. |
| 5,051,109 A | 9/1991 | Simon |
| 5,061,250 A | 10/1991 | Shields |

(Continued)

FOREIGN PATENT DOCUMENTS

| | | |
|---|---|---|
| EP | 0434008 | 6/1991 |
| GB | 2243552 | 11/1991 |
| WO | WO-8904681 | 6/1989 |
| WO | WO-8910767 | 11/1989 |

*Primary Examiner* — Kevin C Sirmons
*Assistant Examiner* — Imani Hayman
(74) *Attorney, Agent, or Firm* — Blank Rome LLP (57) ABSTRACT

Improvements in a safety hypodermic needle and a method of making the same are disclosed. The improvements relate to a commercial embodiment of a patented safety needle and comprise a tubular member extruded from a flexible elastomeric or rubber-like polymeric material. The tubular member is extruded with two ribs extending from the outer wall of the tubular member and spaced apart 90° circumferentially. The wall of the tubular member is provided with through cuts to form a cutout on one wall portion and an elongated lever on the opposite wall portion in the 90° space between the ribs. The cuts separate the wall of the tubular member into two outwardly flexible arms, each having a single rib thereon adjacent an edge of the arm. One end of the tubular member is stretched over the needle hub of a hypodermic needle and the other end is stretched over a needle cup which houses the sharp needle point. The needle cup is provided with a needle opening through which the needle extends during use. After use the flexible arms automatically return the needle cup into a protective position housing the needle point. Latching mechanisms are provided on the hub and lever for releasably holding the arms in a "cocked" position or for permanently holding the arms in a disabled or "safe" condition to prevent inadvertent needle sticks.

18 Claims, 7 Drawing Sheets

(56) References Cited

U.S. PATENT DOCUMENTS

| | | |
|---|---|---|
| 5,078,697 A | 1/1992 | Rammler |
| 5,098,401 A | 3/1992 | De Lange |
| 5,242,417 A | 9/1993 | Paudler |
| 5,250,031 A | 10/1993 | Kaplan et al. |
| 5,256,152 A | 10/1993 | Marks |
| 5,295,972 A | 3/1994 | Mischenko |
| 5,304,148 A | 4/1994 | Lannoye et al. |
| 5,304,192 A | 4/1994 | Crouse |
| 5,348,544 A | 9/1994 | Sweeney et al. |
| 5,531,704 A | 7/1996 | Knotek |
| 5,538,508 A | 7/1996 | Steyn et al. |
| 5,713,872 A | 2/1998 | Feuerborn et al. |
| 5,746,718 A | 5/1998 | Steyn et al. |
| 5,925,020 A | 7/1999 | Nestell |
| 6,409,706 B1 | 6/2002 | Loy |
| 6,918,891 B2 | 7/2005 | Bressler et al. |
| 6,986,759 B1 | 1/2006 | Jeremijevic et al. |
| 7,211,069 B2 | 5/2007 | Lehmann et al. |
| 7,300,423 B2 | 11/2007 | Cocker et al. |
| 7,320,682 B2 | 1/2008 | Cocker et al. |
| 2007/0100296 A1 | 5/2007 | Hwang |

SAFETY NEEDLE AND METHOD OF MAKING SAME

BACKGROUND OF THE INVENTION

1. Field of the Invention

The present invention relates generally to hypodermic syringes and phlebotomy apparatus and more particularly to improvements in a protective cover for the hypodermic needle of disposable hypodermic syringes and phlebotomy apparatus that advantageously prevent inadvertent needle sticks or punctures, both before and after use of the syringe or apparatus.

2. Description of the Prior Art

Infectious diseases can be transmitted to medical personnel and others by way of inadvertent needle sticks or punctures with an infected needle of a hypodermic syringe or phlebotomy apparatus. Cases have been reported in which human HIV (AIDS) infection and other infectious diseases have been transmitted by accidental or inadvertent needle sticks. A number of devices have been developed for the purpose of preventing such needle sticks.

One type of prior art device in common use employs a protective sheath external to the needle which is retractable to permit insertion of the needle into the body of the patient and is then slidable back over the needle past the needle point as, or after, the needle is withdrawn from the body. In some of this type of prior art protective device, a spring or axially resilient sheath is used to extend the sheath over the needle point upon withdrawal of the needle. Several of these prior art devices use a collapsible sheath formed by a plurality of resilient arms surrounding the needle and a needle cup that encloses the needle tip and prevents inadvertent needle sticks. An offset needle opening is provided in the end of the needle cup. The arms are bowable or bendable outwardly away from the needle axis and permit the needle to be guided through the offset opening for use. After use, the arms are movable inwardly toward the needle axis with or without a biasing means to again enclose the needle point within the needle cup. One example of such prior art devices is described in my U.S. Pat. No. 5,256,152.

Another example of such prior art devices is disclosed in U.S. Pat. Nos. 5,538,508 and 5,746,718 issued to Steyn, the entire subject matter of which is incorporated herein by reference. In a commercial embodiment of the Steyn safety needle device, very similar to the embodiment shown in FIGS. 1 and 2 of the Steyn patents, the needle cup is a molded polymeric end cap with an offset needle opening. The collapsible sheath is formed from a length of an extruded flexible polymeric tube with four reinforcing ribs projecting radially from the circumference of the extruded tube and equi-angularly spaced at 90° about the tube circumference. As used herein, the term "rib" or "ribs" is used to describe the longitudinally extending projection(s) from the outer circumference of the tubular member. Except for circumferential portions at the proximal and distal ends of the sheath, two opposing walls of the extruded tube between the ribs are cut out to form two flexible opposing arms, each arm having an extruded rib extending along each of its two edges. One end of the extruded tube is stretched over the needle cup and the other end is stretched over the needle support base. Notches are provided on the inside of the arms midway between the ends of the sheath which are intended to cause the arms to bow outwardly when the tubular member is axially compressed. As the two arms bow outwardly to their maximum extent, they also fold rearwardly toward the syringe barrel so that the user can manually grasp and hold the arms against the syringe barrel when administering an injection.

Although this commercial embodiment of the Steyn safety needle device is operable for its intended purpose, it has several shortcomings that can be eliminated by the improvements disclosed herein according to the present invention. In particular, those shortcomings include: (1) the flexible arms do not reliably flex outwardly when the needle is deployed, but frequently flex inwardly; (2) because of excessive lateral movement of the needle inside the needle cup, the needle point may miss the needle opening and strike the inside face of the end of the needle cup requiring repeated attempts to align the needle with the opening; (3) the user must grasp the needle cup with the fingers of one hand and urge it proximally toward the needle support thereby placing the user's fingers in very close proximity to the needle point and shaft, which could easily cause an inadvertent needle stick and/or contamination of the needle point and shaft; (4) the arms flex outwardly and rearwardly alongside the barrel of the syringe so that the user has only one hand free (one hand is holding the needle cup) to both hold the syringe and grip at least one arm and press it against the surface of the syringe barrel to keep the needle exposed for use, an extremely awkward maneuver; and (5) the device has no means for disabling itself after use to prevent its accidental reuse.

Furthermore, one of the primary shortcomings of many the prior art devices which use protective sheaths of the foregoing type is that during at least some of the period of time between the preparation of the hypodermic syringe for an injection, or the phlebotomy apparatus for entering a vein, and the discarding of the used needle, inadvertent needle sticks of persons other than the patient are still possible.

It would be desirable, therefore, to provide a safety hypodermic needle for use with a disposable hypodermic syringe, as well as for use with catheter needles and other types of body-penetrating hypodermic needles, that overcomes the foregoing limitations and shortcomings of the commercial embodiment of the Steyn safety needle device as well as other prior art devices, has a minimum number of parts, is economical to manufacture and is easy and convenient to use. The present invention overcomes the aforementioned limitations of the commercial embodiment of the Steyn safety needle device and provides still further improvements over those other prior art safety devices for hypodermic needles as will be described in detail in the following specification.

SUMMARY OF THE INVENTION

The present invention is directed to improvements in protective covers for hypodermic needles and, in particular, to improvements in the commercial embodiment of the Steyn safety needle device and in the method of making it to more effectively prevent inadvertent needle sticks and to be more versatile. The safety needle of the invention comprises a needle, typically a hollow, hypodermic needle shaft with a sharp bevel point or tip, a needle support hub into which the needle shaft is inserted and a protective sheath which is affixed at one end to the hub and at least partially encloses the greater part of the longitudinal extent of the needle shaft and completely encloses the needle point in a needle cup until the needle is ready to be inserted in the body. The needle cup has a closed end with a needle opening radially offset from the cup center and through which the needle passes during use.

The protective sheath is preferably cut from a length of an extruded polymeric material, such as silicone rubber, polyethylene, polypropylene or the like, and preferably a clear or transparent rubber-like or elastomeric material. Other manufacturing techniques, such as injection molding, may be employed. The protective sleeve or sheath may also be made of different materials, preferably polymeric materials, and assembled together in its final form. In addition, the protective sheath may be molded or made with regions of different stiffness so that some regions are more or less flexible than others.

The protective sheath is preferably extruded in a generally tubular form with a circular or elliptical cross-section and two radial ribs circumferentially spaced about 90° apart around the outer surface of the extruded tube (as distinguished from the four radial ribs disclosed in the Steyn patents and provided in the commercial embodiment thereof). The extruded tube is then cut to appropriate lengths for assembly with a needle cup at one end of the tube and with a support huh of a needle at the other end of the tube. It has also been found that the two ribs need not extend in a precise radial orientation from the outer circumference of the tubular member, but rather may have other than radial orientations. The number of ribs may also vary so long as they are positioned on the outer circumference of the tubular member as described below.

In the commercial embodiment of the Steyn safety needle device, generally rectangular portions of two opposing walls of the tubular sheath intermediate the ends are completely cut away to provide a pair of outwardly bowable flexible arms, each arm having two extruded radial ribs, one rib extending along each of the two edges of each arm. According to the method and apparatus aspects of the present invention, the 90° wall portion between the ribs, a first wall portion, is cut through along only three sides leaving one narrow side of the first wall portion still attached to the tube at one end for use as a cocking lever to be described further herein. An opposing second wall portion of substantially the same size and circumferential extent as the first wall portion is completely cut away on four sides leaving two flexible arms as in the Steyn device, but with at least one rib extending along the upper edge of each arm. The extruded tube of the invention with at least two outwardly extending ribs, and at least one rib along the upper edge of each arm is cut to appropriate lengths and one end is stretched over the support hub of a hypodermic needle and the other end, to which the cocking lever is attached, is stretched over the proximal end of the needle cup with the center of the offset needle opening of the cup disposed 180° around the tube circumference from the longitudinal axis of the first wall portion and about 135° around the tube circumference from each of at least the two outwardly extending ribs.

According to the present invention, the provision of at least one rib along the upper edge of each flexible arm adjacent the first wall portion or cocking lever and no ribs along the lower edge of each flexible arm causes the arms of the protective sheath to reliably flex outwardly away from the needle axis rather than flex inwardly as frequently occurs with the four-rib construction, i.e., a rib along both upper and lower edges of each flexible arm, of the commercial embodiment of the Steyn device when the needle cup is retracted rearwardly to expose the needle.

As previously mentioned, according to the invention, the first wall portion is used as a cocking lever which is grasped by the user and articulated upwardly, then rearwardly toward the syringe barrel to, first align the needle with the offset needle cup opening, then cause the flexible arms to bow outwardly and guide the needle point through the needle cup opening. The provision of the cocking lever advantageously permits the user to expose the needle for use without having to grasp the needle cup as is necessary when using the patented and commercial embodiments of the Steyn device with the attendant possibility of an inadvertent needle stick. The cocking lever may be provided with a tab attached at the free end of the lever which may be used for holding the cocking lever against the syringe barrel with the protective sheath and needle in the "ready for use" condition. When the needle is inserted in the patient's body, the tab may be released and the medication is injected through the needle. Upon completion of the injection, the needle is withdrawn from the patient's body and the aims automatically return to their unbowed or unflexed condition with the needle cup again enclosing the needle point in the "safe" condition.

Preferably, however, the cocking lever and the needle hub support are provided with first interengaging components to form a manually-operated latching mechanism for securing the protective sheath in its "ready for use" or "cocked" position so that it is unnecessary for the user to hold the cocking lever against the syringe barrel in preparation for giving an injection. Upon giving the injection, the latching mechanism is automatically released when the needle cup engages the patient's body and the flexed arms automatically return to their unbowed or unflexed "safe" condition with the needle cup again enclosing the needle point. The tubular member and/or the cocking lever and/or the needle hub support are preferably provided with second interengaging components for disabling the syringe by securing the protective sheath in the "at rest," unflexed or "safe" condition alter it has been used to prevent inadvertent reuse. With the second interengaging components engaged, the protective sheath cannot be operated to expose the needle point. This disabled condition signifies to medical personnel that the syringe has been used and should be discarded. Also, in this way, a needle which is potentially contaminated with the body fluids of a patient carrying an infectious disease is rendered safe from the standpoint of inadvertent needle sticks.

The needle cup according to the invention is an injection molded component that differs from the needle cup of the commercial embodiment of the Steyn device in that it is provided with a relatively small, generally V-shaped guiding channel to insure that, before the protective sheath is retracted or "cocked" with the cocking lever, the needle shaft is positively guided into alignment with the offset opening in the distal end of the needle cup, unlike the operation of the commercial embodiment of the Steyn device.

The safety needle of the invention can also be used in medical procedures for inserting catheters into blood vessels with a needle, in phlebotomy procedures and in other procedures in which hypodermic needles are used and the danger of inadvertent needle sticks exist.

Although a number of improvements to the Steyn safety needle device are disclosed in the specification and accompanying drawings, it should be understood that, apart from the specific embodiments disclosed herein, this invention is generally applicable to any type of hypodermic needle used to penetrate the body to either introduce a substance into the body or to withdraw a substance from the body, such as blood or other body fluids.

With the foregoing and other objects, advantages and features of the invention that will become hereinafter apparent, the nature of the invention may be more clearly understood by reference to the following detailed description of the invention, the appended claims and to the several views illustrated in the attached drawings.

DETAILED DESCRIPTION OF THE INVENTION

Figure 1:
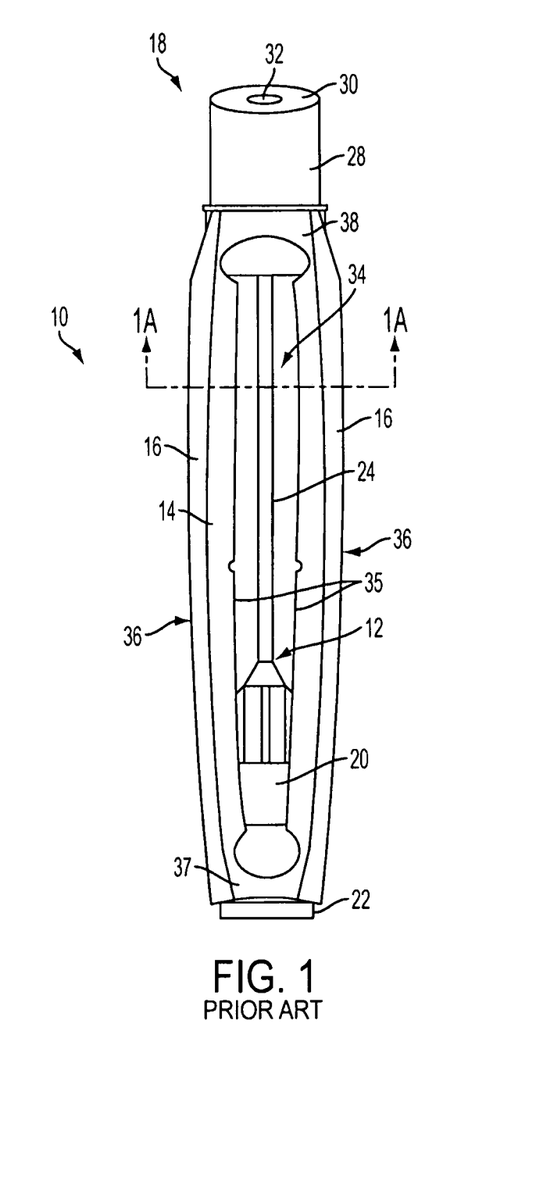
FIG. 1 is a top plan view of the prior art commercial embodiment of the Steyn safety needle device in its "at rest" or unflexed condition.
Figure 1A:
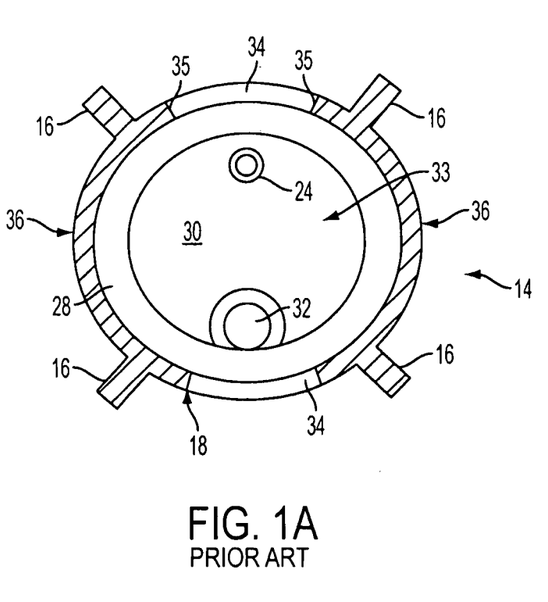
FIG. 1A is a cross-sectional view of the prior all commercial embodiment of the Steyn safety needle device taken along line 1A-1A of FIG. 1.
Figure 2:
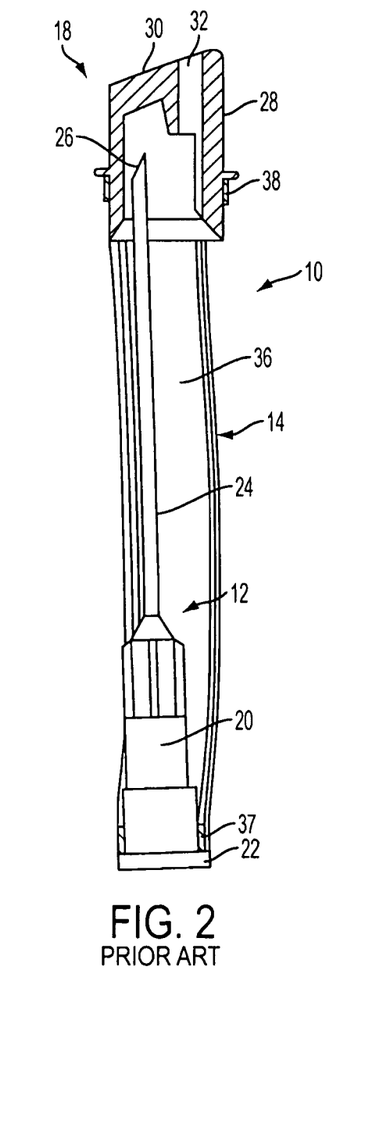
FIG. 2 is a partial longitudinal cross-section of the prior art commercial embodiment of the Steyn safety needle device of FIG. 1.
Figure 3:
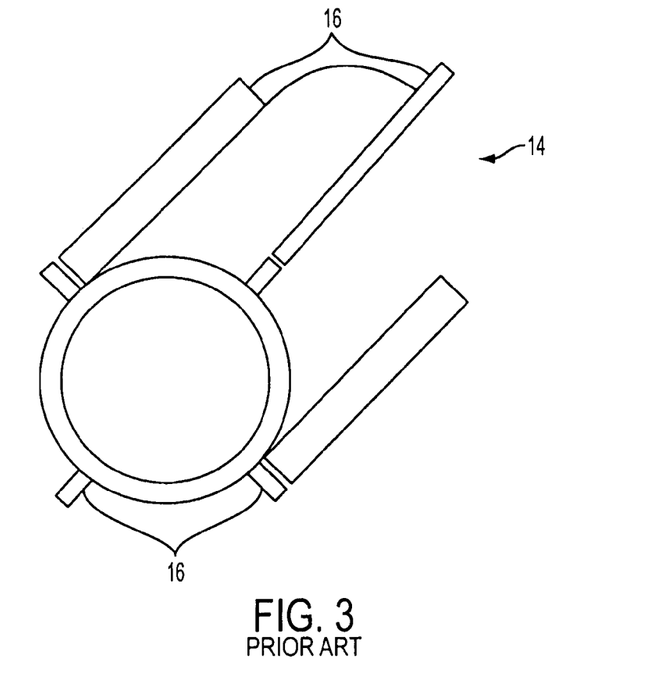
FIG. 3 is a perspective view illustrating a longitudinal section of the extruded elastomeric tube used to construct the prior art commercial embodiment of the Steyn safety needle of FIG. 1.
Figure 4:
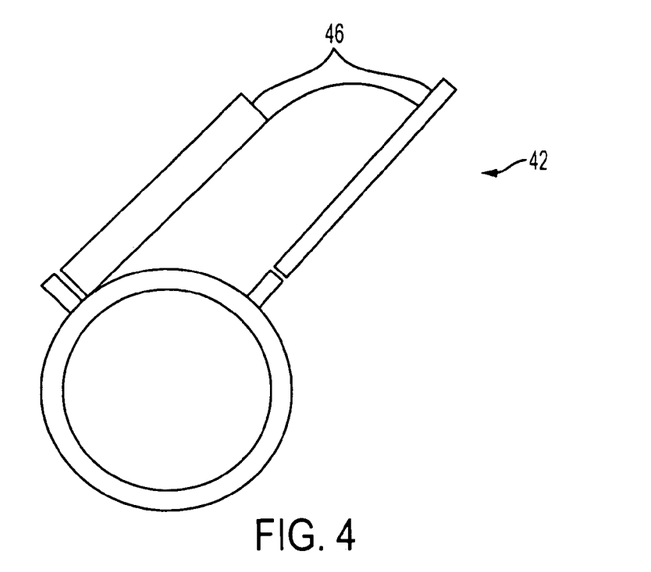
FIG. 4 is a perspective view illustrating a longitudinal section of the extruded tube used to construct the protective sheath of the improved safety needle device of the present invention.

Referring now in detail to the drawings, there is illustrated in FIGS. 1-3 and 1A a prior art commercial embodiment of the Steyn needle protective device 10 substantially as shown in FIGS. 1 and 2 of U.S. Pat. Nos. 5,538,508 and 5,746,718. Device 10 comprises a needle assembly 12, an extruded elastomeric tubular member 14 with four equi-angularly spaced, radial ribs 16 (see also FIG. 3) and a needle cup 18. The needle assembly 12 is conventional and includes a huh 20, an end flange 22 and an elongate hypodermic needle 24 having a beveled point 26 and extending axially from the hub 20. Needle cup 18 is an injection molded member having a tubular wall 28 and a blocking end wall 30 with an elongated opening 32 (FIGS. 1A and 2) through which the needle 24 is adapted to pass. As best shown in the transverse section of FIG. 1A, the axes of the needle 24 and the needle cup 18 are offset so that the needle 24 is misaligned with the opening 32 in the cup cavity 33 to thereby prevent the needle 24 from passing through the opening 32 until the user manually aligns them with the fingers of one hand.

The top and bottom opposing walls of extruded tubular member 14 are provided with longitudinal cut-outs 34 (only the top cutout shown in FIG. 1) that form a pair of flexible arms 36 each with a pair of ribs 16 (FIG. 1A) extending adjacent the upper and lower edges thereof (only upper edges 35 are shown in FIG. 1). One end 37 of the tubular member 14 is stretched over the needle hub 20 and the other end 38 is stretched over the needle cup 18 to assemble the protective needle device 10. Other details of the construction and operation of the protective needle device 10 are described in the aforementioned Steyn patents.

As described above, the commercial embodiment of the Steyn safety needle device 10 has several shortcomings, including: (1) the flexible arms 36 do not reliably flex outwardly when the needle 24 is deployed through opening 32, but frequently flex inwardly; (2) because of excessive lateral movement of the needle 24 inside the needle cup 18 (FIG. 1A), the point 26 of needle 24 frequently misses the needle opening 32 and strikes the inside face of the blocking end 30 of the needle cup 18 requiring repeated attempts by the user to align the needle with the opening; (3) the user must grasp the needle cup 18 with the lingers of one hand and urge it proximally toward the needle huh 20 thereby placing the user's fingers in dangerously close proximity to the needle point 26 and needle 24, which could cause an inadvertent needle stick and/or contamination of the needle point and needle; (4) as the arms 36 flex outwardly and rearwardly alongside the barrel of the syringe (not shown), the user has only one hand free (the other hand is holding the needle cup 18) to both hold the syringe and grip at least one flexible arm 36 and press it against the surface of the syringe barrel to keep the needle exposed for use, an extremely awkward maneuver; and (5) the device 10 has no means for disabling it after use to prevent its accidental reuse.

Referring now to FIGS. 4-5, 5A and 6-8, one embodiment of the improved safety needle device 40 according to the present invention is illustrated. First, referring to FIG. 4, there is shown a section of an extrusion 42 that can be used for the protective sheath or tubular member 44 of the safety needle device 40 of the invention. Extrusion 42 has two radial ribs 46 spaced about 90° apart on the circumference thereof instead of the four ribs 16 of the prior art tubular member 14 shown in FIG. 3 and is preferably extruded from a clear, flexible elastomeric or rubber-like polymeric material, such as silicone rubber. Instead of the two radial ribs 46, other orientations and configurations of the two ribs 46 may be employed.

Figure 5:
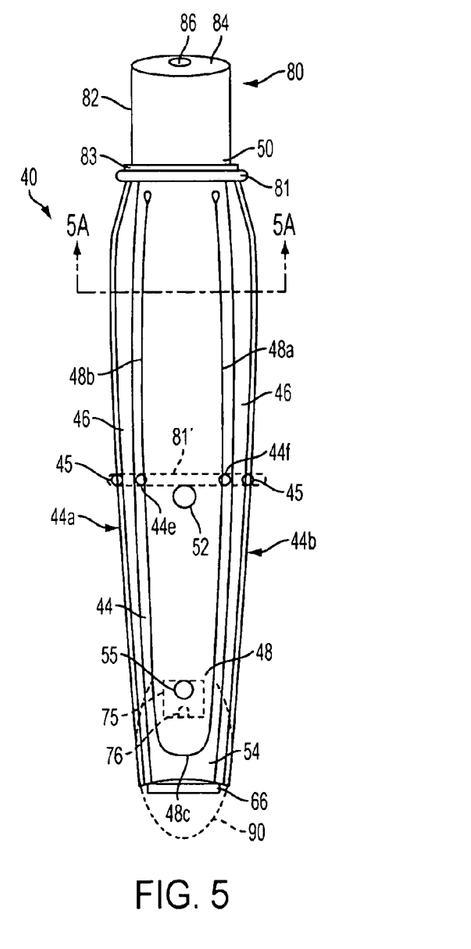
FIG. 5 is a top plan view of one embodiment of the improved safety needle device of the present invention in the initial or "safe" condition.

FIG. 5 is a top plan view of the improved safety needle device 40 (the top of the device 40 as described herein is the circumferential portion of the tubular member 44 that includes the two ribs 46). The top wall of the tubular member 44 between the ribs 46 is cut through along three sides 48a, 48b and 48c as shown in FIG. 5 to form an elongated lever or tab 48 that remains connected to the tubular member 44 only at its distal end 50. Lever 48 is provided with a through hole 52 and a pin 55 along its longitudinal axis for purposes to be described hereinafter.

Figure 6:
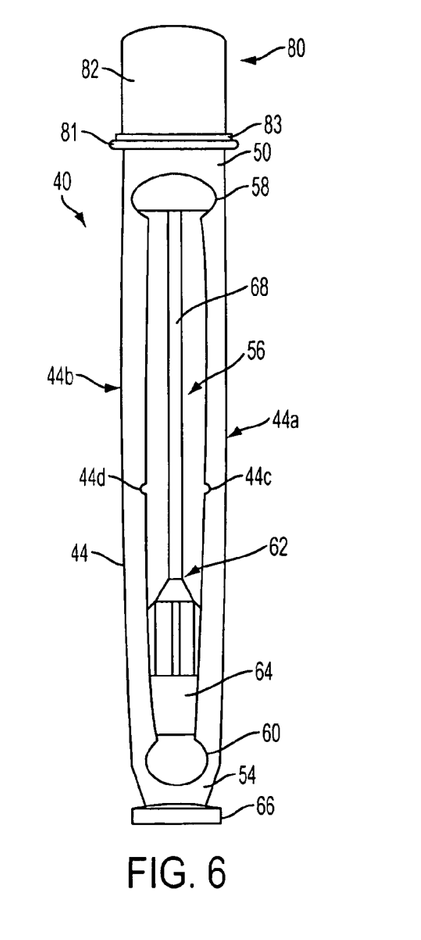
FIG. 6 is a bottom plan view of the FIG. 5 embodiment of the improved safety needle device of the present invention.

FIG. 6 is a bottom plan view of the improved safety needle device 40 (the bottom of the device 40 is the circumferential portion of the tubular member 44 directly opposite the midpoint between the two ribs 46). The bottom wall of the tubular member 44 is cut away from the distal end 50 of the tubular member to its proximal end 54 to form an essentially rectangular cutout 56 with curved ends 58, 60. The circumferential width of the cutout 56 is substantially the same as the circumferential width of the lever 48.

Needle assembly 62 is conventional and includes a hub 64, an end flange 66 and an elongate hypodermic needle 68 having a beveled point 70 extending axially from the hub 64. According to the invention, a latching mechanism 72 (FIG. 7) comprises a sleeve 73 that is slid over mid fastened, e.g., adhesively, to hub 64 of the needle assembly 62. Alternatively, sleeve 73 may be sized so as to be secured to huh 64 with an interference fit. Sleeve 73 has a projection or abutment 75 on the top side thereof that has a circumferential width slightly less than the circumferential width of lever 48 (see FIG. 5). A rearwardly inclined latch pin 76 and a small bore 77 are formed along the longitudinal axis of the abutment 75 for engagement with the hole 52 and disabling pin 55, respectively, as described in more detail hereinafter.

Needle cup 80 is preferably an injection molded member having a cylindrical wall 82 with an external annular flange 83 and a blocking end wall 84 with an opening 86 (FIGS. 5, 5A, 7 and 8) through which the needle 68 is adapted to pass. To assemble the tubular member 44 with the needle assembly 62 and needle cup 80, the distal and proximal ends 50, 54 of the tubular member 44 are stretched over the needle cup 80 and needle hub 64, respectively, up to the respective flanges 83, 66.

Figure 5A:
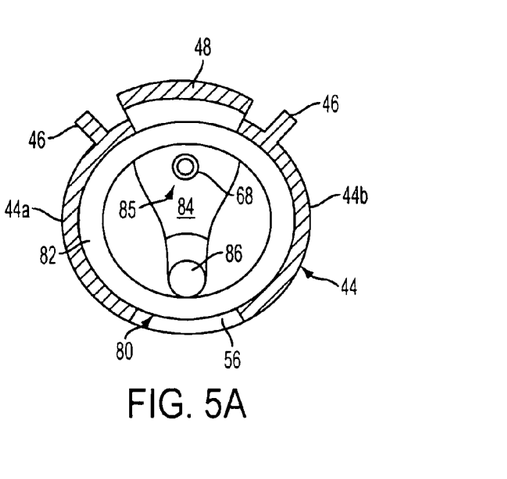
FIG. 5A is a cross-sectional view of the embodiment of the improved safety needle device of the present invention taken along line 5A-5A of FIG. 5.
Figure 7:
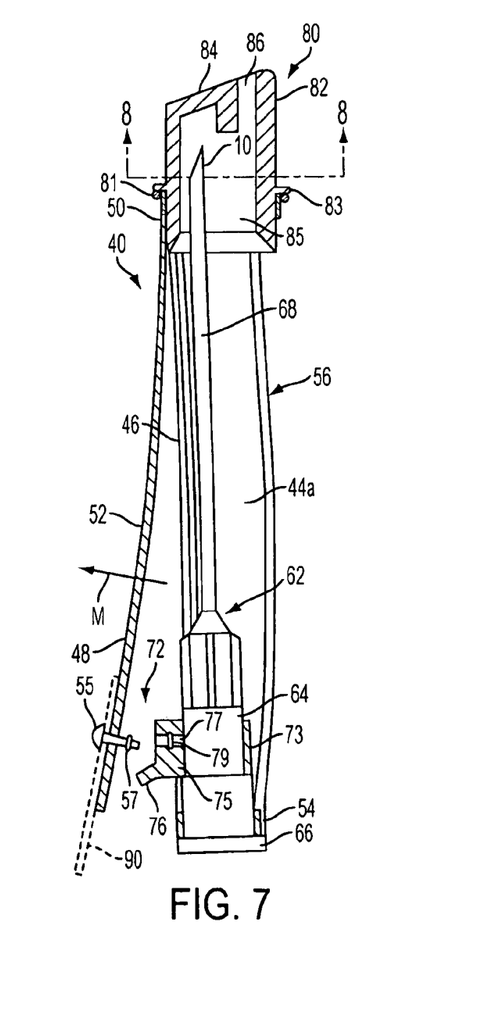
FIG. 7 is a partial longitudinal cross-section of the FIG. 5 embodiment of the improved safety needle device of the present invention.
Figure 8:
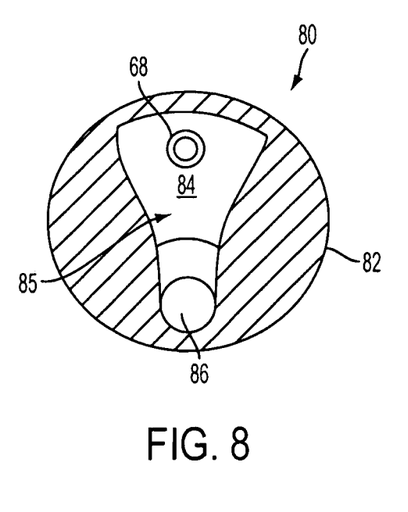
FIG. 8 is a cross-sectional view of the needle cup of the improved safety needle device of the present invention taken along line 8-8 of FIG. 7.

As shown in the partial longitudinal section of FIG. 7 and the cross-sections of FIGS. 5A and 8, the axes of the needle 68 and the needle cup 80 are offset so that the needle point 70 is misaligned with the opening 86 in the cup to thereby prevent the needle 68 from passing through the opening 86 until they are aligned with one another. This misalignment may be effected in at least two ways as explained in the Steyn patents, namely, by cutting off one end of the tubular member at an angle to the longitudinal axis thereof or by leaving a gap between a portion of the end lace of the tubular member 44 and a respective flange 66 or 83. Other ways of effecting the misalignment will be apparent to those skilled in the art.

The bottom cutout 56 and cut sides 48a, 48h and 48c on the top of the tubular member 44 form two outwardly flexible arms 44a, 44b of the remaining two opposing circumferential portions of the tubular member 44. Each flexible arm has one rib 46 extending from the arm adjacent a respective cut side 48a and 48b on the top of the tubular member 44 (FIG. 5). Because each arm 44a, 44h has a rib 46 adjacent the top edge thereof (and no rib on the lower edge thereon, the arms consistently and reliably flex outwardly away from the needle 68 when the needle 68 is aligned with the opening 86 and the cup 80 is moved proximally toward the needle huh 64. Notches 44c, 44d, 44e and 44f may be provided at the midpoint of the upper and lower edges of the arms to aid in causing the arms 44a, 44b to flex at their midpoints rather than at another longitudinal position along the arms. Notches 45 (FIG. 5) may also be provided on the outermost edges of the ribs 46 for a purpose to be hereinafter described.

FIG. 5A is a cross-section of the device 40 and FIG. 8 is a cross section of the needle cup 80 showing the misaligned relationship between the needle 68 and the opening 86 in the initial or "at rest" condition of the safety needle device 40 with the needle 68 confronting the blocking end wall 84. The interior cavity 85 of the needle cup 80 is relatively small in volume compared to the volume of cavity 33 of the cup 18 of the commercial embodiment of the Steyn device. Cavity 85 is also substantially V-shaped in cross-section so as to assist in guiding the needle 68 into the opening 86 when the safety needle device is operated as described below. The shape and small volume of the internal cavity 85 of the needle cup 80 helps prevent the needle point 70 from striking the blocking end face 84 of the needle cup 80 when the needle is guided toward the opening 86. This shape is an improvement over the internal shape of the safety needle device shown in FIG. 6 of the Steyn patents and in the commercial embodiment of the Steyn device.

To operate the improved safety needle device 40 of the invention, the device 40 would typically be attached to a medication-containing syringe (not shown) at the needle hub 64. Holding the syringe in one hand, the user grasps the lever 48 with the lingers of the other hand and moves it upwardly away from the axis of the device as shown by the arrow M in FIG. 7. The position of the abutment 75 beneath the lever 48 raises the lever above the tubular member 44 (see FIG. 7) and facilitates the user grasping the lever.

Importantly, and unlike the Steyn safety needle device, during operation of the device 40 of the invention, the users fingers are safely positioned adjacent the syringe and needle hub 64 and well away from the needle cup 80 so that there is no danger of an inadvertent stick with the needle point 70. Continued movement of the lever 48 first upwardly and then slightly rearwardly causes the arms 44a, 44h to begin to flex outwardly and the needle cup 80 to move relative to the needle 68 and needle point 70 in a direction to align the needle 68 with the opening 86. The internal substantially V-shaped or cavity 85 of the needle cup 80 guides the needle 68 until the needle point 70 is aligned with the opening 86. The user then pulls the lever 48 farther rearwardly (axially) toward the syringe until the flexible arms 44a, 44b flex or bow outwardly to their "cocked" position and the needle 68 passes through the opening 86. It has been found that the flexible arms 44a, 44b more reliably flex outwardly to the "cocked" position when there are extruded ribs 46 adjacent only the top edges of the arms rather than ribs adjacent both the top and bottom edges of the arms as in the Steyn safety needle device.

The user may then use the hand holding the syringe to also grasp the lever 48 thereby freeing the other hand of the user. Preferably, however, the user inserts the latch pin 76 into through hole 52 in the lever 48 to temporarily hold the flexible arms 44a, 44b in their outwardly flexed. "cocked" position with safety needle device 40 ready for use e.g., to administer an injection. As the user administers the injection, the distal end of the needle cup 80 engages the body of the patient and automatically unlatches the latching mechanism 72 by disengaging the pin 76 from the hole 52. Upon withdrawal of the needle from the patient, the flexible arms 44a, 44h automatically return to their unflexed positions shown in FIGS. 5-7 and the needle 68 and needle point 70 return to their "safe" positions inside the tubular member 44 and needle cup 80 as shown in FIG. 7. Should it occur upon withdrawal of the needle from the patient that the pin 76 re-engages the hole 52 in lever 48 and retains the arms in the "cocked" position, the hole 52 and/or the pin 76 may be arranged offset from the longitudinal axis of the device 40 so as to preclude such re-engagement.

After completion of the injection and return of the components to their "safe" positions, the user can then "disable" the device 40 by forcing the disabling pin 55 into bore 77 of the abutment 75. This effectively prevents reuse of the device 40 and warns medical personnel that the device 40 has been used and should be discarded. Preferably, the disabling pin 55 and bore 77 are provided, respectively, with a mating annular ridge 57 and annular groove 79 that prevent removal of the pin 55 from bore 77 once it has been forced therein.

Alternatively, the device 40 may be disabled by a flexible elastomeric ring 81, such as an O-ring, stretched about the distal end 50 of the tubular member 44 adjacent the needle cup flange 83. After use and return of the device components to the "safe" position, the ring 81 may be rolled or shifted proximally to the approximate mid-point of the flexible arms 44a, 44b where it engages the notches 45 in the ribs 46 and positively prevents outward flexing of the arms and exposure of the needle point 70 through opening 86. See ring 81' shown in dashed lines in FIG. 5. Any mechanism that precludes or restrains one or both of the flexible arms 44a, 44b from bowing or flexing outwardly will effectively disable the device 40.

Other embodiments of the lever and latching mechanisms will be apparent to those skilled in the art. For example, as shown in dashed lines in FIG. 5, an enlarged tab 90 may be affixed to the end of lever 48, e.g., with pin 55, to facilitate gripping of the lever 48. One advantage of enlarged tab 90 is that it provides a larger surface area for the user to grasp and cock the device, i.e., by engaging the latch pin 76 with hole 52 or to hold against the barrel of a syringe.

Other arrangements for "cocking" the flexible arms 44a, 44b and "disabling" the device are also possible. For example, a pair of pins may be attached to the lever along its longitudinal axis and two small bores may be provided in the abutment into which one or the other of the pins may be inserted. The flexible arms 44a, 44b may be "cocked" as described above and a first pin inserted into a larger diameter first bore to retain the arms in their "cocked" position until it is automatically unlatched as described above. After the device 40 is used for an injection and the needle 68 automatically returns to its "sate" position, the device may be "disabled" by inserting the second pin into the second bore. To insure that the device 40 is permanently disabled, the second pin and second bore may be provided with interengaging annular serrations or the like to prevent the second pin from being removed from the second bore.

Other forms of latching and disabling mechanisms for holding the device 40 in the "cocked" position or "disabled" position are contemplated, and, in light of the foregoing description, will be apparent to those skilled in the art.

It is to be understood that the terms "initial," "at rest" and "safe" are used herein to describe the initial state, position or condition of the arms 44a, 44b when the safety needle device 40 of the invention is removed from its sterile package, as well as the final state, position or condition of the arms immediately following use of the safety needle device when it is ready to be disabled and discarded.

Although a certain presently preferred embodiment of the invention has been described herein, it will be apparent to those skilled in the art to which the invention pertains that variations and modifications of the described embodiment may be made without departing from the spirit and scope of the invention. Accordingly, it is intended that the invention be limited only to the extent required by the appended claims and the applicable rules of law.

What is claimed is:

1. A safety needle for insertion into a body of a patient comprising a substantially cylindrical tubular member made from a flexible polymeric material, said tubular member having a longitudinal axis, a substantially cylindrical wall, distal and proximal ends, said tubular member having through cuts in said wall on opposite sides thereof extending longitudinally and circumferentially from adjacent the distal end to adjacent the proximal end of the tubular member to form a pair of flexible arms, a needle having a needle axis and a needle point and being mounted in a needle hub with an end flange, the needle hub being mounted in the proximal end of the tubular member, and a substantially cylindrical needle cup having a longitudinal axis and a blocking end wall with a radially offset needle opening therein, the needle cup being mounted in the distal end of the tubular member with the needle and needle opening being radially offset from one another and the needle point confronting the blocking end wall to prevent needle sticks, only two ribs, one of said ribs disposed along the outer surface of a respective flexible arm and extending generally radially outwardly therefrom, the through cuts in one side of said wall comprising longitudinally and circumferentially extending cuts such that the wall portion between the cuts in said one side forms a lever attached to the tubular member at the distal end thereof, said lever having a free end;
wherein said two ribs are circumferentially spaced about 90° from one another on the outer surfaces of said flexible arms, said wall portion forming said lever being disposed in the 90° space between said two ribs.

2. The safety needle according to claim 1, wherein each of said ribs is disposed along a respective edge of one of said flexible arms and adjacent a respective longitudinal cut in said wall.

3. A safety needle for insertion into a body of a patient comprising a substantially cylindrical tubular member made from a flexible polymeric material, said tubular member having a longitudinal axis, a substantially cylindrical wall, distal and proximal ends, said tubular member having through cuts in said wall on opposite sides thereof extending longitudinally and circumferentially from adjacent the distal end to adjacent the proximal end of the tubular member to form a pair of flexible arms, a needle having a needle axis and a needlepoint and being mounted in a needle hub with an end flange, the needle hub being mounted in the proximal end of the tubular member, and a substantially cylindrical needle cup having a longitudinal axis and a blocking end wall with a radially offset needle opening therein, the needle cup being mounted in the distal end of the tubular member with the needle and needle opening being radially offset from one another and the needle point confronting the blocking end wall to prevent needle sticks, only two ribs, one of said ribs disposed along the outer surface of a respective flexible arm and extending generally radially outwardly therefrom, the through cuts in one side of said wall comprising longitudinally and circumferentially extending cuts such that the wall portion between the cuts in said one side forms a lever attached to the tubular member at the distal end thereof, said lever having a free end;
wherein said lever is adapted to be moved proximally and away from said needle to cause the flexible arms to bow outwardly from an at rest position to a cocked position and the needle axis to align with the needle opening in the blocking end wall, the proximal movement of said lever causing the needle to extend through the needle opening in the cocked position of the flexible arms, and including first interengaging means on said lever and said needle hub for latching the flexible arms in the cocked position and for automatically releasing the flexible arms from the cocked position;
said safety needle further including second interengaging means on said lever and said needle hub for latching the flexible arms in the at rest position to thereby disable the safety needle from use.

4. The safety needle according to claim 3, wherein said second interengaging means comprises a disabling pin mounted adjacent the free end of said lever and a mating bore on said needle hub.

5. The safety needle according to claim 4, wherein said second interengaging means comprises the disabling pin mounted adjacent the free end of said lever and a sleeve affixed to said hub, said sleeve having a bore for receiving said disabling pin to thereby disable the safety needle from use.

6. The safety needle according to claim 5, wherein said disabling pin and said bore are provided with mating means for permanently preventing disengagement of said disabling pin from said bore to thereby disable the safety needle from use.

7. A safety needle for insertion into a body of a patient comprising a substantially cylindrical tubular member made from a flexible polymeric material, said tubular member having a longitudinal axis, a substantially cylindrical wall, distal and proximal ends, said tubular member having through cuts in said wall on opposite sides thereof extending longitudinally and circumferentially from adjacent the distal end to adjacent the proximal end of the tubular member to form a pair of flexible arms, a needle having a needle axis and a needlepoint and being mounted in a needle hub with an end flange, the needle hub being mounted in the proximal end of the tubular member, and a substantially cylindrical needle cup having a longitudinal axis and a blocking end wall with a radially offset needle opening therein, the needle cup being mounted in the distal end of the tubular member with the needle and needle opening being radially offset from one another and the needle point confronting the blocking end wall to prevent needle sticks, only two ribs, one of said ribs disposed along the outer surface of a respective flexible arm and extending generally radially outwardly therefrom, the through cuts in one side of said wall comprising longitudinally and circumferentially extending cuts such that the wall portion between the cuts in said one side forms a lever attached to the tubular member at the distal end thereof, said lever having a free end;

wherein said needle cup has an internal cavity with a substantially V-shaped internal wall as viewed in a cross section transverse to the longitudinal axis of the needle cup with the needle opening disposed at the bottom of said cross section.

8. A safety needle for insertion into a body of a patient comprising a hypodermic needle having a needle axis and a needle point and being mounted in a needle hub, a substantially cylindrical tubular member extruded from a flexible polymeric material, said tubular member having a longitudinal axis, a substantially cylindrical wall, distal and proximal ends, said tubular member having through cuts in said wall on opposite sides thereof extending longitudinally and circumferentially from adjacent the distal end to adjacent the proximal end of the tubular member to form on one side a lever with a free end and on the other opposite side a cutout, said through cuts further forming only two flexible arms, each arm having only one rib extending longitudinally thereof and generally radially outwardly therefrom, said ribs being circumferentially spaced apart about 90°, the needle hub being mounted in the proximal end of the tubular member, and a substantially cylindrical needle cup having a longitudinal axis and a blocking end wall with a radially offset needle opening therein, the needle cup being mounted in the distal end of the tubular member with the needle and needle opening being radially offset from one another and the needle point confronting the blocking end wall to prevent needle sticks, the needle opening being positioned on that side of the tubular member opposite the lever.

9. The safety needle according to claim 8, wherein said lever is adapted to be moved proximally away from said needle and rearwardly to cause the flexible arms to bow outwardly from an at rest position to a cocked position and the needle axis to align with the needle opening in the blocking end wall, the proximal movement of said lever causing the needle to extend through the needle opening in the cocked position of the flexible arms, and including first interengaging means on said lever and said needle hub for releasably latching the flexible arms in the cocked position.

10. The safety needle according to claim 9, wherein said first interengaging means comprises a first through hole intermediate the length of said lever and a latch pin on said needle hub.

11. The safety needle according to claim 9, including second interengaging means on said lever and said needle hub for latching the flexible arms in the at rest position to thereby disable the safety needle from use.

12. The safety needle according to claim 11, wherein said second interengaging means comprises a disabling pin adjacent the free end of said lever and a bore on said needle hub.

13. The safety needle according to claim 8, wherein said needle cup has an internal cavity with a substantially V-shaped internal wall as viewed in a cross section transverse to the longitudinal axis of the needle cup with the needle opening disposed at the bottom of said cross section.

14. The safety needle according to claim 8, including an enlarged tab affixed to said lever at the free end thereof.

15. The safety needle according to claim 9, including second interengaging means for disabling the safety needle from use, said second interengaging means comprising a ring mounted on said tubular member adjacent said needle cup, said ring being adapted to move axially over said tubular member so as to grip and hold said flexible arms in their at rest position.

16. A safety needle for insertion into a body of a patient comprising a hypodermic needle having a needle axis and a needle point and being mounted in a needle hub, a substantially cylindrical tubular member formed from an elastomeric polymeric material, said tubular member having a longitudinal axis, a substantially cylindrical wall, distal and proximal ends, said tubular member having through cuts in said wall on opposite sides thereof extending longitudinally and circumferentially from adjacent the distal end to adjacent the proximal end of the tubular member to form on one side a lever with a free end and on the other opposite side a cutout, said through cuts further forming a pair of flexible arms, each arm having only one rib extending longitudinally thereof and generally radially therefrom, said ribs being circumferentially spaced apart about 90°, the needle hub being mounted in the proximal end of the tubular member, and a substantially cylindrical needle cup having a longitudinal axis and a blocking end wall with a radially offset needle opening therein, the needle cup being mounted in the distal end of the tubular member with the needle and needle opening being radially offset from one another and the needle point confronting the blocking end wall to prevent needle sticks, the needle opening being positioned on that side of the tubular member opposite the lever.

17. A safety needle for insertion into a body of a patient comprising a hypodermic needle having a needle axis and a needle point and being mounted in a needle hub, a substantially cylindrical tubular member formed from an elastomeric material, said tubular member having a longitudinal axis, a substantially cylindrical wall, distal and proximal ends, said tubular member having through cuts in said wall on opposite sides thereof extending longitudinally and circumferentially from adjacent the distal end to adjacent the proximal end of the tubular member to form on one side a lever with a free end and on the other opposite side a cutout, said through cuts further forming a pair of flexible arms, each arm having a rib extending longitudinally thereof and generally radially therefrom, the needle hub being mounted in the proximal end of the tubular member, and a substantially cylindrical needle cup having a longitudinal axis and a blocking end wall with a radially offset needle opening therein, the needle cup being mounted in the distal end of the tubular member with the needle and needle opening being radially offset from one another and the needle point confronting the blocking end wall to prevent needle sticks, the needle opening being positioned on that side of the tubular member opposite the lever, said needle cup having a substantially V-shaped internal cavity as viewed in a cross section transverse to the longitudinal axis of the needle cup, the apex of such V-shaped internal cavity extending from the needle opening.

18. A safety needle for insertion into a body of a patient comprising a hypodermic needle having a needle axis and a needle point and being mounted in a needle hub, a substantially cylindrical tubular member formed from an elastomeric material, said tubular member having a longitudinal axis, a substantially cylindrical wall, distal and proximal ends, said tubular member having through cuts in said wall on opposite sides thereof extending longitudinally and circumferentially from adjacent the distal end to adjacent the proximal end of the tubular member to form on one side a lever with a free end and on the other opposite side a cutout, said through cuts further forming a pair of flexible arms, the needle hub being mounted in the proximal end of the tubular member, and a needle cup having a longitudinal axis and a blocking end wall with an offset needle opening therein, the needle cup being mounted in the distal end of the tubular member with the needle and needle opening being offset from one another and the needle point confronting the blocking end wall to prevent needle sticks, the needle opening being positioned on that side of the tubular member opposite the lever, said needle cup having a substantially V-shaped internal cavity as viewed in a cross section transverse to the longitudinal axis of the needle cup, the apex of such V-shaped internal cavity extending from the needle opening.

\* \* \* \* \*